United States Patent

Sasaki et al.

[11] 4,212,881
[45] Jul. 15, 1980

[54] STREPTOVARICIN C DERIVATIVES

[75] Inventors: Kazuya Sasaki, Higashi Kurume; Hiromi Mitsui, Tokyo; Kazukiyo Onodera, Nagareyama, all of Japan

[73] Assignee: Kaken Chemical Company, Limited, Tokyo, Japan

[21] Appl. No.: 3,802

[22] Filed: Jan. 16, 1979

[30] Foreign Application Priority Data

Feb. 17, 1978 [JP] Japan .................................. 53-16408

[51] Int. Cl.² .................. A61K 31/395; C07D 491/08
[52] U.S. Cl. ..................................... 424/275; 424/279; 260/239.3 P
[58] Field of Search .................. 260/239.3 P; 424/275, 424/279

[56] References Cited

U.S. PATENT DOCUMENTS

| | | | |
|---|---|---|---|
| 3,954,737 | 5/1976 | Rinehart et al. | 260/239.3 P |
| 4,031,215 | 6/1977 | Sasaki et al. | 260/239.3 P |

FOREIGN PATENT DOCUMENTS

| | | | |
|---|---|---|---|
| 50-160289 | 12/1975 | Japan | 260/239.3 P |
| 51-56497 | 5/1976 | Japan | 260/239.3 P |
| 51-129522 | 5/1976 | Japan | 260/239.3 P |
| 51-98285 | 8/1976 | Japan | 260/239.3 P |
| 51-108083 | 9/1976 | Japan | 260/239.3 P |

*Primary Examiner*—Alan L. Rotman
*Assistant Examiner*—Robert T. Bond
*Attorney, Agent, or Firm*—Oblon, Fisher, Spivak, McClelland & Maier

[57] ABSTRACT

Streptovaricin C derivatives having the formula

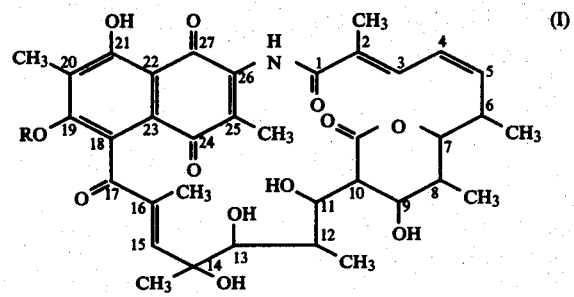

wherein R represents an allyl, cycloalkyl or adamanthyl group or a $C_1$-$C_{20}$ alkyl group which can be substituted with hydroxyl, cyano, acetyl, formyl, furoyl, thenoyl, alkoxy, carbamyl, phenyl or substituted phenyl group or a phenacyl group which can be substituted with a halogen, alkoxy or phenyl group.

2 Claims, 1 Drawing Figure

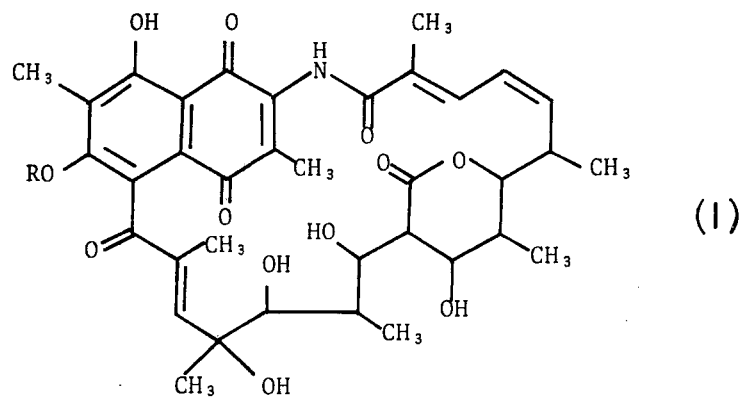
(I)
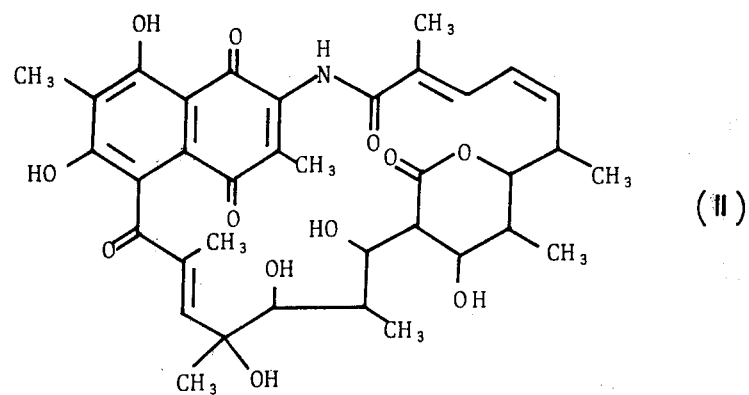
(II)
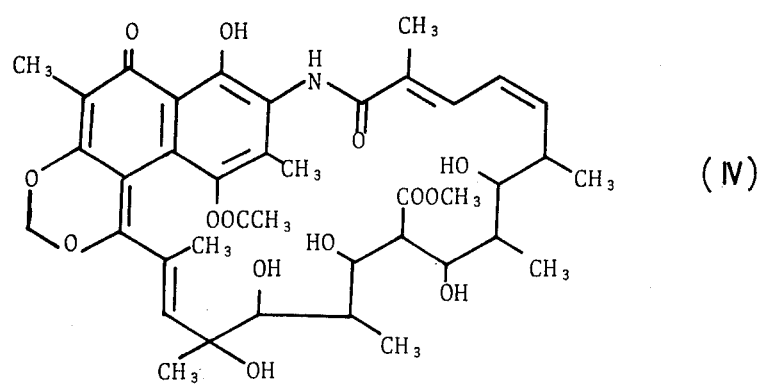
(IV)

STREPTOVARICIN C DERIVATIVES

BACKGROUND OF THE INVENTION

1. Field of the Invention

The present invention relates to novel streptovaricin C derivatives and a preparation thereof and antiviral compositions containing the same as an active ingredient.

2. Description of the Prior Arts

Streptovaricin C is antituberclosis antibiotic produced by culturing the strain of Streptomyces 101, species 2494 and has the chemical formula

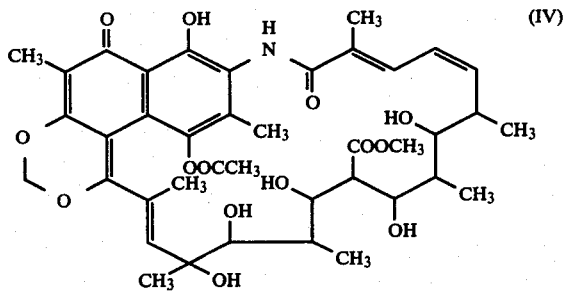

as disclosed in Journal of Antibiotics Vol. 25, Page 71, (1971); Journal of American Chemical Society Vol. 93, Page 6273, (1971) Vol. 93, Page 6275, (1971).

The streptovaricin C is hydrolyzed in a mild oxidizing condition, damavaricin C and atropisodamavaricin Fc can be obtained as disclosed in Journal of Antibiotics Vol. 29, Page 201, (1976) by K. L. Reinhardt.

The inventors have studied on alkaline hydrolyzed products obtained from streptovaricin C have been studied in detail and have found damavaricin Fc together with damavaricin C and atropisodamavaricin Fc.

Atropisodamavaricin Fc is an optical isomer of damavaricin Fc.

In a thin layer silical gel chromatography, they could not be isolated each other to give a single spot.

The inventors have found the optical isomer of damavaricin Fc by a proton NMR spectrum. Damavaricin Fc has P-helicitic structure (natural form) wherein a double bond of C(15)=C(16) is disposed at upper side of carbonyl group C(24)=O in stereomatic structure to the single bond C(17)-C(18) as that of streptovaricin C whereas atropisodamavaricin Fc has M-helicitic structure (non-natural form) wherein the double bond is stereomatically in opposite position (See the report by Reinhardt and helicity principle disclosed in Angewante Chemie International Ed. Vol. 5, Page 385, (1966) ).

SUMMARY OF THE INVENTION

It is an object of the present invention to provide novel streptovaricin C derivatives which have excellent antiviral activity.

It is another object of the present invention to provide a process for producing these novel streptovaricin C derivatives having excellent antiviral activity.

The foregoing and other objects of the present invention have been attained by providing novel antivirus of streptovaricin C derivatives having the formula

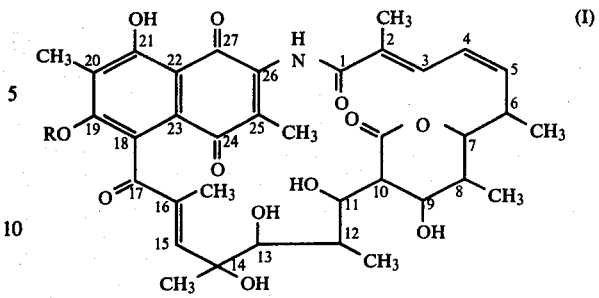

wherein R represents unsubstituted and substituted alkyl group, allyl group, cycloalkyl group, adamanthyl group or unsubstituted and substituted phenacyl group.

DETAILED DESCRIPTION OF PREFERRED EMBODIMENTS

The inventors have produce many derivatives from the compound having the formula (II)

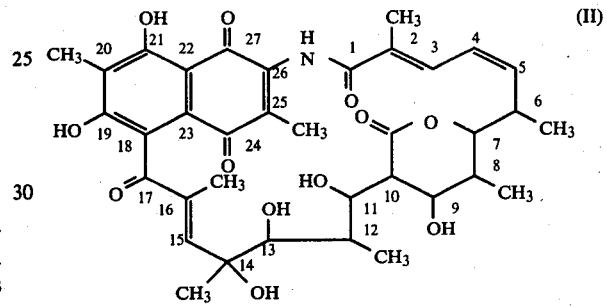

which is damavaricin Fc and its optical isomer of atropisodamavaricin Fc and have studied on effects for inhibiting reverse-transcriptase or RNA-directed DNA-transcriptase of RNA tumor virus of mouse Sarcoma virus in characteristic and have found that ether derivatives obtained by etherifications at 19 position of phenolic hydroxyl group of damavaricin Fc and have excellent effect for the inhibition.

The present invention is to provide novel streptovaricin C derivatives having the formula (I) which are produced by hydrolyzing streptovaricin C in alkaline condition and etherifying phenolic hydroxyl group at 19 position of the resulting product of damavaricin Fc or its optical isomer of atropisodamavaricin Fc.

In the formula (I), R can be allyl and adamanthyl group and also a $C_1-C_{20}$ alkyl group such as methyl, ethyl, propyl, butyl, pentyl, hexyl, heptyl, octyl, nonyl, decyl, undecyl, dodecyl, tridecyl, tetradecyl, pentadecyl, hexadecyl, heptadecyl and octadecyl group. The alkyl group can have substituent of hydroxy, cyano, acetyl, formyl, furoyl, thenoyl, alkoxy, or carbamyl group or unsubstituted and substituted phenyl group. The cycloalkyl group include cyclohexyl or cyclopentyl group. The phenacyl group can have a substituent, such as halophenacyl, alkoxyphenacyl, or phenylphenacyl group.

The novel streptovaricin C derivatives having the formula (I) can be produced by etherification of phenolic hydroxyl group at 19 position of the compound having the formula II.

The etherification can be carried out as follows.

The compound having the formula (II) is reacted with a halide having the formula R-Hal     (III)

wherein R is defined above and Hal is a halogen atom, in suitable solvent in the presence of silver oxide.

Suitable halides (III) include chlorides, bromides and iodides.

The solvent is preferably an inert solvent in the reaction, such as methanol, ethanol, acetone, 1,2-dimethoxyethane, and tetrahydrofuran.

The starting material having the formula (II) is dissolved or dispersed in the solvent and about 0.5 to 5 mole equivalent of silver oxide is added to the solution or the dispersion and the mixture is thoroughly stirred at room temperature for 30 minutes to 5 hours to form a silver salt. Suitable amount especially excess of the halide having the formula (III) is added to the suspension of the silver salt under stirring to carry out a condensation.

The reaction is usually carried out at room temperature and the reaction time is depending upon the halide (III) and is usually about 30 minutes to 24 hours. Thus, the novel streptovaricin C derivatives (I) which are obtained by etherification of phenolic hydroxyl group at 19 position of the starting material (II).

The novel streptovaricin C derivatives having an alkoxy group at 19 position in the formula (I) can be obtained by dissolving or dispersing an alkali metal salt preferably potassium salt of the compound having the formula (II) in acetone and adding the halide having the formula (III) and reacting them at room temperature for about 1 to 24 hours.

The isolation and purification of the object compound (I) can be carried out by the conventional processes. For example, after the reaction, the reaction mixture is filtrated through Celite to separate the silver halide and the filtrate is concentrated and dried at 35° to 45° C. in vacuum and the residue is dissolved in an organic solvent and the product is purified by a chromatography and/or a recrystallization.

The novel streptovaricin C derivatives (I) are yellow or yellowish orange crystalline compounds and substantially water-insoluble but soluble to organic solvents such as methanol, ethanol, acetone, halohydrocarbons, esters, ethyl ether, tetrahydrofuran, dioxane, 1,2-dimethoxyethane, dimethylsulfoxide, dimethylformamide, and benzene.

When the compounds (I) are treated with a reducing agent such as hydrosulfite, dithionite, zinc-acetic acid or ascorbic acid, the colors are changed to pale yellow but the products are easily converted to the object compounds (I) by contacting the product with oxygen, air or an oxidizing agent and the colors are changed to the original yellow or yellowish orange. The object compounds (I) can be easily converted to alkali metal salts thereof and the aqueous solutions thereof are substantially neutral.

The starting material of the compound (II) is one of streptovaricin derivatives called as damavaricins. The preparations of damavaricin C derivatives are disclosed in Japanese Unexamined Patent Publication Nos. 160289/1975, 56497/1976, 56498/1976, 98285/1976 and 108083/1976.

However, damavaricin Fc derivatives and atropisodamavaricin Fc derivatives have not been disclosed in any prior art and the object compounds (I) are compounds.

The novel streptovaricin C derivatives (I) of the present invention have effects for inhibiting reverse-transcriptase activity of RNA tumor virus of mouse Sarcoma virus (See Experiments). The reverse-transcriptase is reported by Temin and Baltimore in Nature Vol. 226, Page 1211, (1970) and Vol. 226, Page 1209, (1970). It has been found that the reverse-transcriptase RNA tumor virus directly concerns to cancerogenics for animal cells, and it is enzyme needed for autopropagation of RNA tumor virus.

The streptovaricin C derivatives (I) also have effect for inhibiting focus formation of kidney cells of rats caused by murine Sarcoma virus. Accordingly, the novel streptovaricin C derivatives (I) have a characteristic of anticancerogenic virus to inhibit cancerogenic step of animal cells and are useful as antiviral agents.

Acute toxicity of the novel streptovaricin C derivatives (I) are remarkably low level. For example, 19-O-methyl compound (I) has $LD_{50}$ to mouse of more than 1000 mg/kg in intramuscular injection and more than 3000 mg/kg in oral dose.

The antiviral composition containing the streptovaricin C derivative (I) as an active ingredient is also one feature of the present invention.

In the antiviral composition, the compound (I) can be pure optical isomer as damavaricin Fc form and atropisodamavaricin Fc form and a mixture of optical isomers thereof, and a mixture of two or more compounds (I) having different substituent R.

The novel streptovaricin C derivative (I) can be used with any adjuvant, but it is preferably used as a composition prepared by admixing a solid or liquid organic or inorganic adjuvant.

Suitable adjuvants include water, gelatin, lactose, starch, calcium celluloseglycolate, microcrystalline cellulose, stearly alcohol, magnesium stearate, talc, vegetable oil, benzyl alcohol, propylene-glycol, gum, polyalkyleneglycol, white mineral oil, jelly and cholesterol.

The compositions can be various forms such as powder, tablet, granule, sugar coated tablet, suppository, pill, capsule, solution, suspension, ampoule, emulsion and injective. These compositions can be prepared by incorporating suitable adjuvant such as preservatives, stabilizers, wetting agents, emulsifiers, dissolution accelerator, osmotic pressure adjusting salts, buffers, binders, suspending and dispersing agents and lubricants, in the conventional processes.

The novel streptovaricin C derivatives (I) can be used as medicines for human as well as veterinary medicines in said forms.

In the therapeutic use of the streptovaricin C derivatives (I), a dose is depending upon an administration, kind of patient, age and body weight and it is usually in a range of 1 to 100 mg/kg preferably 5 to 50 mg/kg in non-oral administration and in a range of 1 to 1000 mg/kg preferably 25 to 500 mg/kg in oral administration.

Certain examples for producing typical streptovaricin C derivatives having the formula (I) will be illustrated for purposes of illustration only.

EXAMPLE 1

19-O-methyl compound:

Into 40 ml of methanol, 350 mg of atropisodamavaricin Fc (containing about 25% of damavaricin Fc) was dissolved and 176 mg of silver oxide was added and the mixture was stirred at room temperature for 1 hours to obtain a silver salt of the starting materials.

To the reaction mixture, 2 g of methyl iodide was added and the mixture was stirred at room temperature for 30 minutes and the precipitate of silver iodide was separated by filtering through sellite and the filtrate was concentrated and dried under a reduced pressure to obtain a red oily product. The oily product was recrystallized from ethanol-n-hexane (1:1) to obtain 254 mg of orangish yellow crystalline product of 19-O-methyl-atropisodamavaricin Fc (containing 19-O-methyl damavaricin Fc).

Melting point: 210°-212° C.
Elementary Analysis: $C_{37}H_{45}NO_{12} \cdot 2H_2O$

|  | C | H | N |
|---|---|---|---|
| Calculated (%) | 60.72 | 6.74 | 1.91 |
| Found (%) | 60.50 | 6.42 | 1.72 |

IR Spectrum (carbonyl region)
$\gamma KBr(cm^{-1})$ 1740, 1728, 1670, 1650, 1625
Mass Spectrography: m/e
695 (molecula ion) 677, 659, 643, 641, 625, 623
Ultraviolet Spectrum
$\lambda_{max}^{CH3OH}$(nm) 218, 265, 417

EXAMPLE 2

19-O-benzyl compound:

Into 20 ml of methanol, 200 mg of atropisodamavaricin Fc (containing about 25% of damavaricin Fc) was dissolved and 100 mg of silver oxide was added and the mixture was stirred at room temperature for 5 hours. The resulting suspension of silver salt was concentrated and dried under a reduced pressure and the reside was suspended in 20 ml of tetrahydrofuran and 800 mg of benzyl bromide was added and the mixture was stirred at room temperature for 20 hours. The precipitate of silver bromide was separated by filtering through sellite and the filtrate was concentrated and dried under a reduced pressure. The residue was dissolved in a small amount of chloroform and a large amount of n-hexane was added to obtain yellowish brown precipitate of the crude object compound. The crude product was eluted by a column chromatography of silica gel with 5% methanol-chloroform.

Suitable fractions were collected and concentrated under a reduced pressure and the residue was recrystallized from chloroform-n-hexane (1:1) to obtain 90 mg of yellow crystalline product of 19-O-benzyl atropisodamavaricin Fc (containing 19-O-benzyl damavaricin Fc).

Melting poing: 149°-151° C.
Elementary Analysis: $C_{43}H_{49}NO_{12}$

|  | C | H | N |
|---|---|---|---|
| Calculated (%) | 66.91 | 6.40 | 1.81 |
| Found (%) | 66.80 | 6.59 | 1.60 |

IR Spectrum (carbonyl region):
$\gamma KBr(cm^{-1})$ 1740, 1725, 1680, 1675, 1645, 1625
Mass Spectrography: m/e
771 (molecular ion) 753, 735, 719, 701, 681, 663, 645, 629, 610
Ultraviolet Spectrum:
$\lambda_{max}^{CH3OH}$ (nm) 211, 263, 410

EXAMPLE 3

Into 50 ml of methanol, 340 mg of atropisodamavaricin Fc (containing about 25% of damavaricin Fc) was dissolved and 36 mg of potassium carbonate was added and the mixture was stirred at room temperature for 1 hour to obtain potassium salt. The reaction mixture was concentrated and daCl aqueous solution and was dried over anhydrous sodium sulfate for one night. The solution was concentrated and dried under a reduced pressure. The residual red oily product was eluted by a column chromatagraphy of silica gel with 10% methanol-chloroform.

Suitable fractions were collected and concentrated under a reduced pressure and the residural orangish red oily product was recrystallized from ethanol-n-hexane (1:1) to obtain 158 mg of organish yellow crystalline product of 19-O-formylmethyl-atropisodamavaricin Fc (containing 19-O-formylmethyldamavaricin Fc).

Melting point: 211°-213° C.
Elementary Analysis: $C_{38}H_{45}NO_{13} \cdot 2H_2O$

|  | C | H | N |
|---|---|---|---|
| Calculated (%) | 60.07 | 6.50 | 1.84 |
| Found (%) | 59.71 | 6.37 | 1.75 |

IR Spectrum (carbonyl region):
$\gamma KBr(cm^{-1})$ 1738, 1725, 1680, 1673, 1647, 1625
Proton NMR Spectrum (100 MHz CDCl$_3$):
$\delta^{CHO}$(ppm) 9.60 (s) 9.80 (s)
Ultraviolet Spectrum:
$\lambda_{max}^{CH3OH}$ (nm) 218, 265, 420

The other streptovaricin C derivatives having the formula (I) shown in Table 1 were produced in accordance with the processes of Examples 1 to 3.

Table 1

| Example | R | Melting point (°C.) | Ultraviolet spectrum CH$_3$OH$_{(nm)}$ $\lambda_{max}$ |
|---|---|---|---|
| 4 | ethyl | 191–194 | 218, 264, 418 |
| 5 | n-propyl | 207–209 | 219, 267, 417 |
| 6 | n-butyl | 173–176 | 216, 262, 410 |
| 7 | n-pentyl | 170–172 | 218, 264, 418 |
| 8 | n-hexyl | 175–177 | 218, 264, 418 |
| 9 | n-heptyl | 151–153 | 217, 264, 418 |
| 10 | n-octyl | 169–171 | 219, 264, 419 |
| 11 | n-nonyl | 139–142 | 217, 262, 418 |
| 12 | n-decyl | 138–141 | 218, 264, 418 |
| 13 | n-undecyl | 131–133 | 218, 263, 419 |
| 14 | n-tridecyl | 122–125 | 217, 263, 418 |
| 15 | n-pentadecyl | 117–119 | 217, 263, 415 |
| 16 | n-octadecyl | 117–119 | 217, 264, 418 |
| 17 | isopropyl | 127–130 | 216, 261, 420 |
| 18 | isobutyl | 168–170 | 218, 263, 420 |
| 19 | isoamyl | 175–178 | 217, 262, 420 |
| 20 | allyl | 192–195 | 216, 264, 418 |
| 21 | cyclopentyl | 181–183 | 220, 263, 421 |
| 22 | cyclohexyl | 135–138 | 218, 264, 420 |
| 23 | 1'-adamanthyl | 160–162 | 213, 256, 390* |
| 24 | acetonyl | 193–195 | 217, 265, 418 |
| 25 | 4'-hydroxy-n-butyl | 156–159 | 218, 264, 418 |
| 26 | 3'-cyano-n-propyl | 175–177 | 211, 264, 360* |
| 27 | methoxymethyl | 175–177 | 217, 264, 418 |
| 28 | p-nitrobenzyl | 186–188 | 213, 267, 410 |
| 29 | phenethyl | 171–174 | 264, 417 |
| 30 | phenacyl | 189–191 | 248, 263*, 418 |
| 31 | 2'-formylethyl | 200–203 | 218, 264, 420 |
| 32 | p-chlorophenacyl | 191–193 | 209, 258, 418 |
| 33 | p-methoxyphenacyl | 170–173 | 216, 270, 390* |
| 34 | p-phenylphenacyl | 185–187 | 277, 420 |
| 35 | 2'-furoylmethyl | 196–198 | 219, 272, 397* |
| 36 | 2'-thenoylmethyl | 191–193 | 211, 264, 417 |

Table 1-continued

| Example | R | Melting point (°C.) | Ultraviolet spectrum CH$_3$OH$_{(nm)}$ $\lambda_{max}$ |
|---|---|---|---|
| 37 | carbamylmethyl | 208–211 | 214, 264, 417 |

Note:
*shoulder

EXAMPLE 38

Each of 2500 g of the product of Example 1, 1375 g of lactose, 775 g of microcrystalline cellulose and 375 g of calcium celluloseglycolate was seived through 16 mesh sieve and they were uniformly mixed and changed into a kneader and 3 liters of 3% hydroxypropyl cellulose solution (isopropyl alcohol: water = 3:7) was added and the mixture was kneaded. The mixture was granulated through an extruder granulatoesium stearate was mixed with the granules and the mixture was punched to form tablets.

EXAMPLE 39

Into water, 0.3 g of sodium carboxymethylcellulose and 0.29 g polyvinylpyrrolidone were dissolved to prepare about 20 ml of solution and then, 70 ml of 80% sorbitol was added and 5 g of the product of Example 2 which was pulverized in a ball mill, was added and 80% sorbitol was added to prepare 100 ml of the mixture. The mixture was uniformly dispersed by a homogenizer to prepare syrup.

Experiment

Effect for inhibiting reverse-transcriptase of mouse Sarcoma virus.

The effect for inhibition was determined as follows:
(a) Sample solution:
  Methanol solution containing each active ingredient at a concentration of 6 mg/ml.
(b) Enzyme solution:
  Solution containing 240 μg of virus protein (MLV-moloney) in 1 ml of a buffer solution of 20 mM-tris-hydrochloric acid (pH 7.8), 0.1 M-sodium chloride and 1 mM of dithiotersitol (DTT).
(c) Reaction medium:
  Reaction medium containing 46 mM tris-hydrochloric acid (pH 8.1) 92 mM potassium chloride, 15.4 mM manganese chloride, 0.77 mM-dATP, 0.77 mM-dCTP, 0.77 mM-dGTP, 0.23 μM-3H-TTP (50 ci/mM), 7.7 mM-DTT and 0.038% NP-40.

The reaction mixture was prepared by sequentially admixing (a) 5 μl, with (b) 30 μl and (c) 65 μl and the mixture was thoroughly mixed and kept at 0° C. for 5 minutes. Then, the reaction mixture was kept at 37° C. for 60 minutes and 1 ml of cold 10% trichloroacetic acid solution was added to the reaction mixture to stop the reaction. The mixture was kept at 0° C. for 20 minutes and an insoluble components were collected on each Whatman's paper GF/c (diameter of 2.5 cm) and washed with 5 ml of cold 5% trichloroacetic acid. The residue was dried in an oven at 80° C. and charged in a viral bottle containing 10 ml of toluene solution containing scintillator PPO-POPOP, and radioactivity was measured by a scintillation spectrometer.

The results are shown in Table 2.

Table 2

Effect for inhibiting reverse-transcriptase of mouse Sarcoma virus by the streptovaricin C derivatives (I) (300 μg/ml).

| R | Percent inhibition (%) |
|---|---|
| methyl | 41 |
| ethyl | 60 |
| n-propyl | 52 |
| n-butyl | 78 |
| n-pentyl | 52 |
| n-hexyl | 60 |
| n-octyl | 41 |
| n-undecyl | 78 |
| cyclohexyl | 45 |
| allyl | 65 |
| benzyl | 67 |
| phenacyl | 50 |
| acetonyl | 58 |

What is claimed is:

1. A Streptovaricin C derivative having the formula:

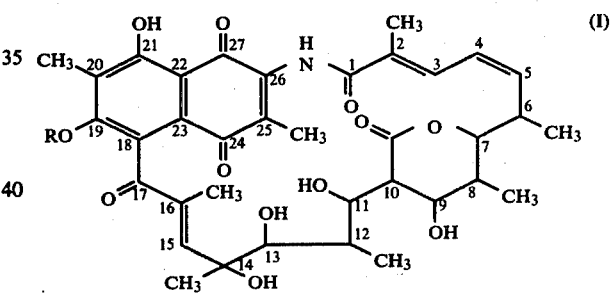

wherein R represents an allyl, cyclopentyl, cyclohexyl or adamanthyl group or a $C_1$–$C_{20}$ alkyl group which can be substituted with hydroxyl, cyano, acetyl, formyl, furoyl, thenoyl, methoxy, carbamyl, phenyl or phenyl group substituted with nitro or ethyl or a phenacyl group which can be substituted with a halogen, methoxy or phenyl group.

2. An antiviral composition comprising an antivirally effective amount of a compound of claim 1 and an adjuvant.

* * * * *